United States Patent [19]

Ohta et al.

[11] 4,068,932

[45] Jan. 17, 1978

[54] OPTICAL INSTRUMENT FOR EXAMINING THE EYE FUNDUS

[75] Inventors: Shinichi Ohta, Tokyo; Isao Matsumura, Yokohama; Kazunobu Kobayashi, Yokohama; Haruhisa Madate, Yokohama, all of Japan

[73] Assignee: Canon Kabushiki Kaisha, Tokyo, Japan

[21] Appl. No.: 687,645

[22] Filed: May 18, 1976

[30] Foreign Application Priority Data

May 23, 1975 Japan .................................. 50-61522
Feb. 24, 1976 Japan .................................. 51-19137
Feb. 24, 1976 Japan .................................. 51-19313

[51] Int. Cl.² .............................................. A61B 3/14
[52] U.S. Cl. ........................................ 351/7; 351/9; 351/13; 351/16; 354/62
[58] Field of Search .................... 351/7, 9, 13, 14, 16; 354/62

[56] References Cited

U.S. PATENT DOCUMENTS 3,217,622  11/1965  Kiyono .................................. 351/7
3,925,793  12/1975  Matsumara ......................... 351/7 X

FOREIGN PATENT DOCUMENTS 1,127,947  12/1956  France .................................. 351/7

OTHER PUBLICATIONS

"Color Photography . . . Fundus," J. Biological Photographic Assoc., 12-1941, pp. 119-135.

Primary Examiner—Paul A. Sacher
Attorney, Agent, or Firm—Toren, McGeady and Stanger

[57] ABSTRACT

The present invention relates to an optical instrument for examining the eye fundus which is so designed that in the optical system including an objective lens visible, targets are built for orientating the visual line of the eye to be inspected along the direction convenient for the inspection of the desired part of the eye fundus in order to be able to inspect the desired part. The visible targets are located at the position conjugate to the eye fundus with regard to the optical system including the objective lens in order that the light beam coming from the targets through the objective lens reaches the eye to be inspected. The image of the visible targets is formed on the eye fundus of the eye to be inspected while the eye to be inspected observes the visible targets through the objective lens in such a manner that the visual line is oriented in the direction along which the targets are seen.

18 Claims, 18 Drawing Figures

OPTICAL INSTRUMENT FOR EXAMINING THE EYE FUNDUS

BACKGROUND OF THE INVENTION

The present invention relates to an optical instrument for inspecting the eye fundus, including visible targets for orienting the visual line of the eye to be inspected along the desired direction.

The optical instrument for examining the eye fundus is so designed that the image of the eye fundus of the eye to be inspected is formed by means of the imaging lens system whereby the formed image is directly observed through the eye piece or recorded on the photographic film. Thus in order to inspect a desired part of the eye fundus, it is necessary that there should be a corresponding angle between the imaging lens system and the visual line of the eye to be inspected. Further in case a plural number of the parts of the eye fundus are to be inspected, it is necessary that the visual line of the eye to be inspected should be oriented along a plural number of the directions in accordance with the number of the parts to be observed. Thus, the eye fundus inspection device is provided with a visual target in order that the visual line of the eye to be inspected could be oriented along the direction corresponding to the parts of the eye fundus to be inspected. The visual line of the eye to be inspected is oriented along the desired direction while the patient observes the visual target.

On the other hand, in the case of the conventional eye fundus inspection device, such as an eye fundus camera, the above mentioned visual target is generally provided movably outside of the frame of the device body. The patient observes the visual target manually brought into a proper position by the operator, whereby the target is observed by the eye of the patient, not opposite to the imaging lens system. Thus the fact that the visual lines of both eyes move correspondingly to each other is made use of. The operator should judge the angle between the visual line of the eye to be inspected and the optical axis of the imaging lens system by means of the relation of the other eye than that to be inspected to the target, which is correlatively independent of the relation of the eye to be inspected to the imaging lens system so that it is difficult to decide the position at which the target is provided. If the patient is squint-eyed, it is furthermore difficult for the operator to decide the position. It is also troublesome work for the operator to carry out the focussing operation of the imaging lens system and at the same time to bring the target into the proper position with the hand stretched.

SUMMARY OF THE INVENTION

A purpose of the present invention is to provide an optical instrument for examining the eye fundus so designed that the visual line of the eye to be inspected is oriented along the direction along which the image of the desired part of the eye fundus is formed, the visible target being observed by the eye to be inspected.

Another purpose of the present invention is to provide an optical instrument for examining the eye fundus so designed that the visible target can be observed at least through the objective lens system of the imaging lens system in such a manner that the optical relation of the visual line of the eye to be inspected to the optical axis of the imaging lens system in order to obtain the image of the desired part of the eye fundus to be inspected.

Another purpose of the present invention is to provide an optical instrument for examining the eye fundus so designed that the visual line of the eye to be inspected can be oriented along the desired direction in a simple way.

A still further purpose of the present invention is to provide an optical instrument for examining the eye fundus which is so designed that the instrument can be operated easily, without being disturbed by the oriented operation of the visual line of the eye to be inspected.

DESCRIPTION OF THE PREFERRED EMBODIMENT

Figure 1:
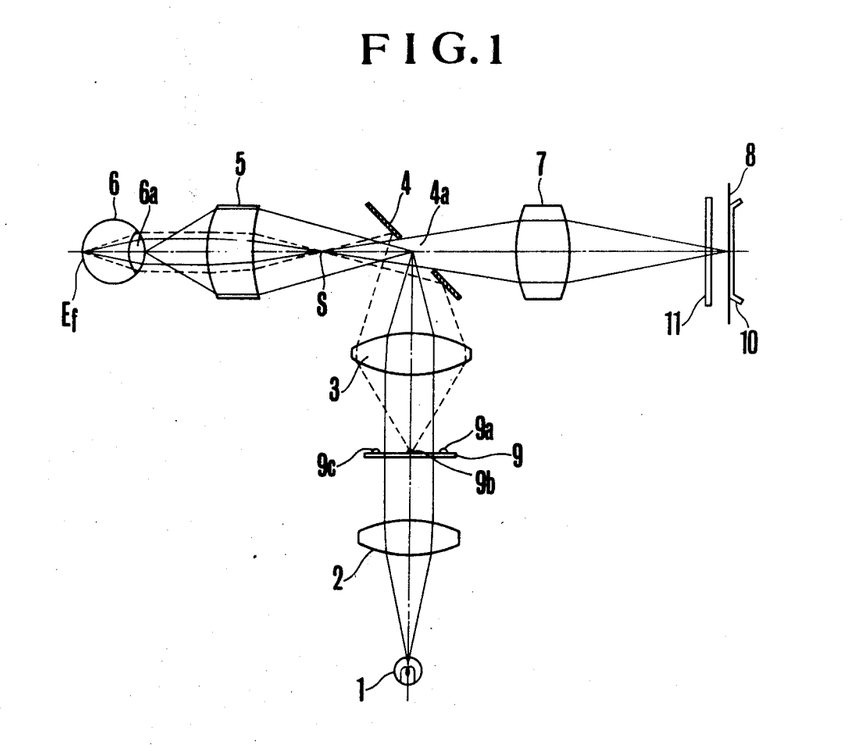
FIG. 1 shows an embodiment of the present invention.
Figure 8:
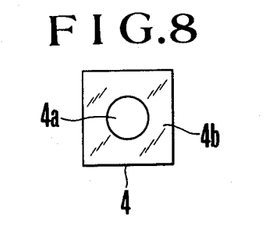
FIG. 8 shows the mirror presenting a hole shown in FIGS. 1, 2, 3, 4, 6 and 7.

In FIG. 1, the light source 1 such as a tungsten lamp is provided at the focal point of the collimating lens 2. The light beam coming from the light source 1 through the lens 2 passes through the relay lens 3. On the focal plane of the lens 3, the image of the light source 1 is formed. At the position at which the image is formed, a mirror 4 presenting a permeable part 4a at the center and a reflecting part 4b around the part 4a as is shown in FIG. 8 is provided at a slant. The light beam coming from the light source 1 and reflected by the mirror 4 with a hole is condensed on the cornea of the eye 6 to be inspected by means of the objective lens 5 so as to illuminate the eye fundus Ef.

The beam reflected at the eye fundus Ef is refracted by means of the eye lens 6a and the lens 5 in such a manner that the image of the eye fundus Ef is once formed at a position S between the lens 5 and the mirror, and then directed toward the relay lens 7 through the hole 4a of the mirror 4. The lens 7 serves to transfer the image formed at the position S to the photosensitive film 8. The film 8 is provided at the position at which the image of the eye fundus Ef is formed, being held by a conventional film holding means 10 including a press plate. The conventional shutter 11 provided between the lens 7 and the film 8 is opened during the necessary time so as to expose the film 8. 9a, 9b and 9c are the visual targets provided in a proper interval from each other on the support body 9 along the direction across the path of the illumination light beam. For these targets 9a, 9b and 9c, the light emissive diodes to be explained later are applied, whereby only a desired diode is lighted up. The targets 9a, 9b and 9c are provided at the position at which the image of the eye fundus Ef on the eye 6 to be inspected is formed through the lenses 5 and 3, namely at the position conjugate to the eye fundus Ef in the optical path including the lens 5, the mirror 4 and the lens 3. In other words, the images of the targets 9a, 9b and 9c are formed on the eye fundus Ef of the eye 6 to be inspected.

Figure 15A:
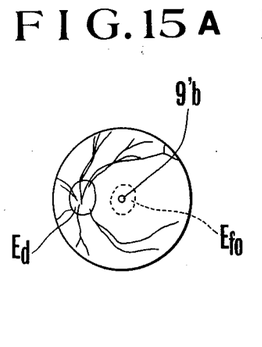
FIGS. 15A, 15B and 15C respectively show the relation between the position of the visible target and the eye fundus to be investigated.
Figure 15B:
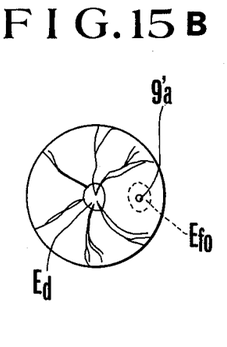
Figure 15C:
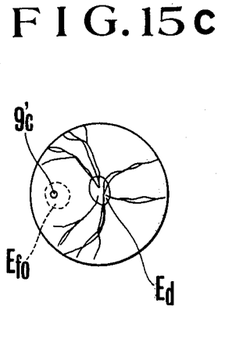

As is shown in FIGS. 15A, 15B and 15C, when the eye 6 to be inspected observes the targets, the images 9'a, 9'b and 9'c of the targets are formed on the yellow spot Ed of the eye fundus Ef. When the target 9b is lighted up, the eye fundus is photographed in such a manner that the fovea comes to the center of the picture as is shown in FIG. 15A, when the target 9a is lighted up the eye fundus of the left eye is photographed in such a manner that the fovea Efo is to the right while the disc Ed comes to the center of the picture as is shown in FIG. 15B, while when the target 9c is lighted up, the eye fundus of the right eye is photographed in such a manner that the fovea Efo is to the left which the disc Ed comes to the center of the picture as is shown in FIG. 15C.

Figure 2:
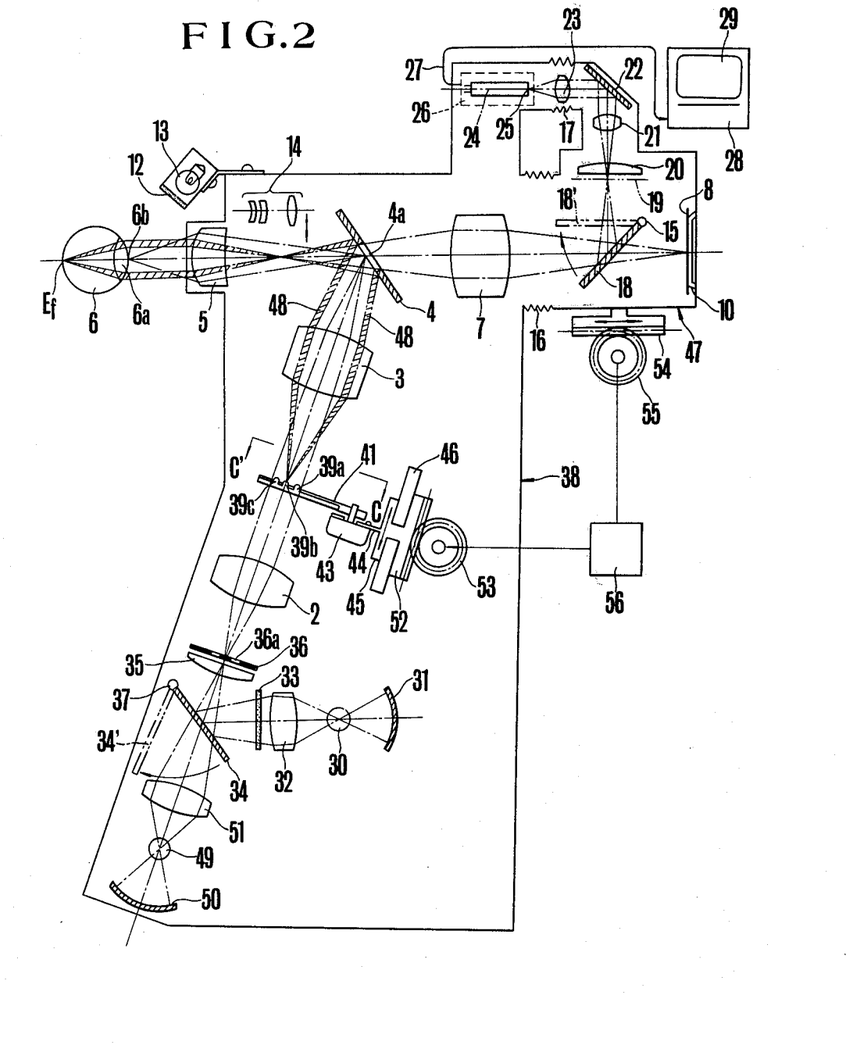
FIG. 2 shows another embodiment of the present invention.

FIG. 2 shows an eye fundus camera which is so designed that an ultra red ray or a very weak light beam is made of as the illumination light beam in order to obtain the focus of the eye fundus or determine the photographic positions. Such light beam hardly gives the irritating effect to the visual nerve of the eye to be inspected so that the pupil of the eye to be inspected can be dilated in a natural way without applying the agent by taking a photograph in a dark place.

When the front part 6b of the eye 6 to be inspected is observed in FIG. 2, in order to make the position of the pupil of the eye to be inspected coincide with the optical axis of the optics of the eye fundus camera the front 6b of the eye 6 to be inspected is illuminated with the illumination light beam coming from the light source 13 for illuminating the front part of eye, including a filter 12 allowing the permission of the ultra red ray or the near ultra red ray. At this time, an auxiliary lens 14 for determining the position of the front part of eye is inserted into the optical path between the objective lens 5 and the mirror 4 with a hole. The light beam reflected at the front part 6b of eye passes through the objective lens 5, the hole 4a of the mirror 4 and the relay lens 7 so as to be reflected by the movable mirror 18 provided slantly on the optical axis in such a manner that an image is formed on the image plane 19 in the air. In the same way as in case the of the conventional movable mirror of the single reflex camera, the mirror 18 is raised up to the position 18' shown in dotted lines around the shaft 15 during the exposure. Having pased through the field lens 20 and the relay lens 21, the image formed on the plane 19 is reflected by the mirror 22 so as to be formed on the photoconductive surface of the pick up tube 24 sensitive in the wave band of the ultra red or the near ultra red ray. The image is converted into an electrical signal by means of the conventional electronic circuit of the TV camera and displayed in the display part 29 of the monitor 28 through the signal route 27. The operator engages in coinciding the pupil of the eye to be inspected with the optical axis of the optical system, while observing the image of the eye front part in the display part 29. During the observation of the eye fundus, the auxiliary lens 14 is brought out of the optical path between the objective lens 5 and the mirror 4 by means of a change over means (not shown in the drawing). Behind the light source 30 such as a tungsten lamp for observation a concave mirror 31 is provided in such a manner that the center of the curvature of the mirror coincides with the light source 30. The light beam coming from the light source 30 passes through the condenser lens 32, is reflected by the movable mirror 34 provided slantly in the optical path, passes through the field lens 35 and condenced on the slit plate 36. A filter 33, allowing the passage of only the ultra red ray, and the near ultra red ray is provided in the optical path between the mirror 34 and the condenser lens 32. Further in the same way as in the case of the movable mirror of the conventional single reflex camera, the mirror 34 is rotated into the position shown in the dotted line 34' around the shaft during the exposure of the film in such a manner that the light beam from the light source 30 does not reach the eye 6 to be inspected. A speed light device 49 radiating a visible light beam is made use of for exposing the film. Behind the speed light device 49, the concave mirror 50 is provided in such a manner that the center of the curvature of the mirror coincides with the speed light tube. When the mirror 34 is rotated into the position 34' shown in the dotted line around the shaft 37, the light beam coming from the speed light is condensed on the slit plate 36 by means of the condenser lens 51 and the field lens 35. The slit plate 36 presents a ring slit 36a in such a manner that the light beam coming from the light sources 30 and 49 through the slit 36a illuminates the eye fundus Ef of the eye 6 to be inspected. By means of the collimating lens 2 and the relay lens 3 the image of the ring-slit 36a is formed at the position at which the mirror 4 with a hole is situated. Further, by means of the objective lens 5, the image of the ring-slit 36a is formed again on the cornea of the eye 6 to be inspected.

At the time of focusing, the movable mirrors 18 and 34 are at the positions shown in the solid line in the drawing in such a manner that the image of the eye fundus by means of the ultra red ray reflected at the eye fundus Ef is formed on the photoconductive surface 25 of the pick up tube. While observing the image of the eye fundus in the monitor 28, the observer focusses the optical system at the eye fundus Ef and determines the photographic positions of the eye fundus. At the time of taking a photograph the movable mirrors 18 and 34 are rotated respectively into the positions 18' and 34' by means of the shafts 15 and 37, whereby the speed light tube 49 radiates the light beam, which is reflected at the eye fundus Ef so as to expose the photosensitive film 8.

At the time of determining the photographic positions of the eye fundus Ef the visible target 39a, 39b and 39c are provided at the position at which the image of the eye fundus Ef is formed by means of the lenses 5 and 3 in the optical path of the effective illumination light beam between the lenses 2 and 3 namely at the position conjugate to the eye fundus. Thus the light beam coming from a target reaches the eye fundus Ef so as to form the image of the target there as is shown in 48.

Figure 9:
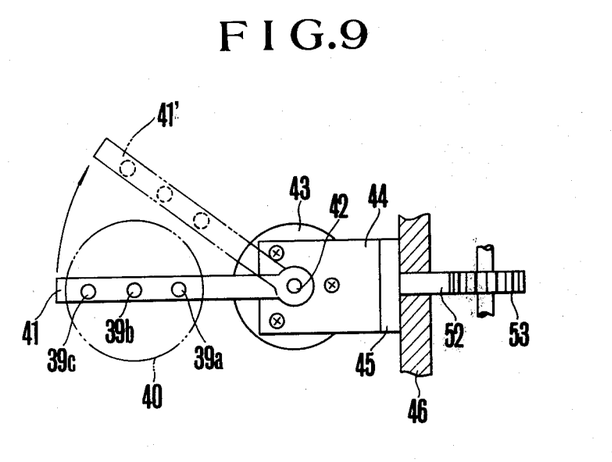
FIG. 9 shows an example of the visible target used in the embodiments of the present invention.

FIG. 9 shows the target part seen along the C-C' direction in FIG. 2, whereby the targets 39a, 39b and 39c which are the light emissive diodes are fixed in a certain interval from each other on the arm 41 so as to be able to take pictures of the eye fundus as is shown in FIGS. 15A, 15B and 15C. The arm 41 is fixed on the shaft 42 of the magnetic spool 43 so as to be withdrawn out of the effective illumination light beam 40 into the position shown in the dotted line 41' at the time of the exposure of the film 8 and returned to the initial position after the exposure by means of the operation of the magnetic spool 43. On the other hand, the magnetic spool 43 is fixed on the projection 44 of the slide member 45. This slide member 45 is slidably engaged with the guide member 46. The guide member 46 serves to guide the slide member 45 along a direction parallel to the optical axis of the lenses 2 and 3. On the slide member 45, a rack 52 is fixed so as to be engaged with the pinion 53.

On the other hand the casing 47 in which the movable mirror 18, the lens 21, the film holding member 10 and so on are built, is connected, by means of the bellows 16 and 17, with the casting 38 in which the light sources 30 and 49, the lenses 2, 3, 5, 7 and 23, the targets 39a, 39b and 39c, the pick up tube 24 and so on are built, whereby the casing 47 is slidable along the direction of the optical axis of the lens 7 by means of the rack 54 fixed on the casing 47 and the pinion 55 engaged with the rack 54. The optical system is focussed at the eye fundus of the eye to be inspected while the casing 47 is slided by rotating the above mentioned pinion 55. Hereby the rotation of the pinion 55 is transferred to the pinion 53 by means of the gear train 56. The pinion 53 is rotated in functional engagement with the rotation of the pinion 55 for focussing so as to always bring the targets 39a, 39b and 39c at the position conjugate to the eye fundus Ef. In this way, the eye to be inspected can always recognize the target clearly by means of the focussing operation of the photographic system even when the visibility of the eye alters during the inspection or several patients with different visibilities are inspected.

Figure 12:
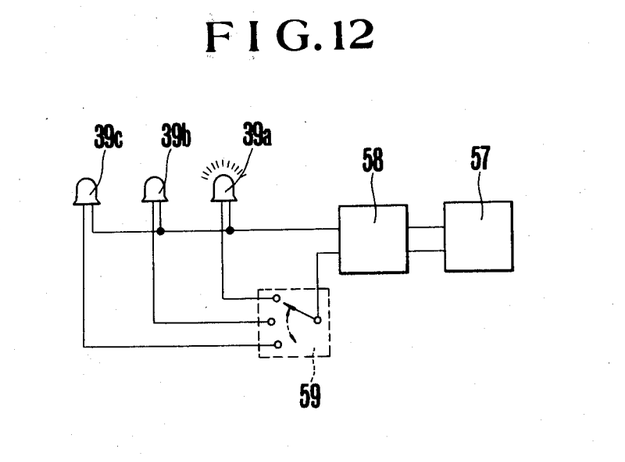
FIG. 12 shows a control unit for controlling the lighting of the target shown in FIGS. 9 and 10.

It targets 39a, 39b and 39c are the light emissive diodes whose switching on and off is controlled by a means shown in FIG. 12. The output of the light source 57 is applied to the means for producing an intermittent current with several Hz, whereby the output of the means is applied to the targets 39a, 39b and 39c through the change over switch 59 presenting an input terminal and three output terminals. By changing over the switch 59, it is possible to light up the desired target. The target twinkles with several Hz so that the attention of the patients is attracted. It is desirable that the targets 39a, 39b and 39c issue the light weak enough not to cause the contraction of the pupil of the eye to be inspected and that the targets 39a, 39b and 39c issue green light conjugate to the red light or the light beam with the range of the wave length between 5000–6000A in order to increase the contrast because the eye fundus is illuminated with the ultra red or the near ultra red ray during the observation.

Figure 10:
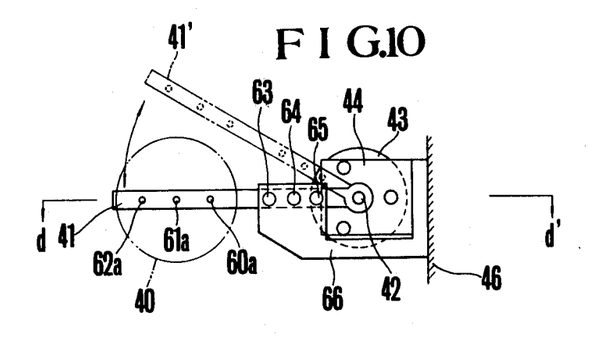
FIG. 10 shows another example of the visible target used in the embodiments of the present invention.
Figure 11:
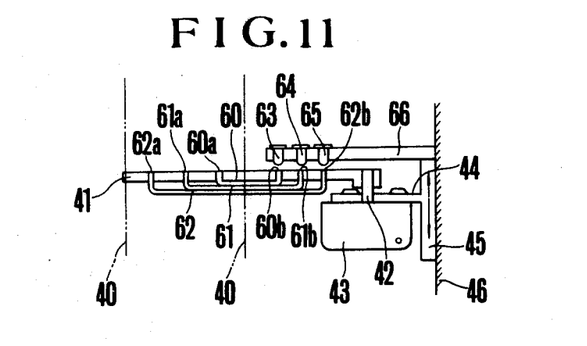
FIG. 11 shows a section of FIG. 10 along the $d$–$d'$ direction.

The target part shown in FIG. 10 or shown in d-d' section in FIG. 11 is an improvement made in such a manner that the repeated deformation and the breakage of the conductor for the current supply is eliminated. In fact, the target shown in FIG. 9 presents the light emissive diodes directly upon the arm whereby the current supply conductors are subject to the repeated deformation and breakage.

In the same way as explained in accordance with FIG. 2 and FIG. 9 a magnetic spool 43 is fixed on the slide member 46 slidably engaged in the guide member 46. On the arm 41 fixed on the rotary shaft 42 of the magnetic spool 43 the optical fiber bundles 60, 61 and 62 are provided. The light emissive faces 60a, 61a and 62a of the bundles 60, 61 and 62 are provided in a similar interval from each other as in case of the targets shown in FIG. 9. Further the light incident faces 60b, 61b and 62b of the bundles 60, 61 and 62 are provided out of the optical path of the effective illumination light beam 40. These light incident faces 60b, 61b and 62b are respectively directed toward the lamps 63, 64 and 65 when the arm 41 is brought into the light beam 40. The lamps 63, 64 and 65 are provided on the arm 66 fixed on the slide member 45, so as to be moved as one body with the magnetic spool 43. The lamps 63, 64 and 65 are switched on and off by means of the same control means as that shown in FIG. 12.

Figure 3:
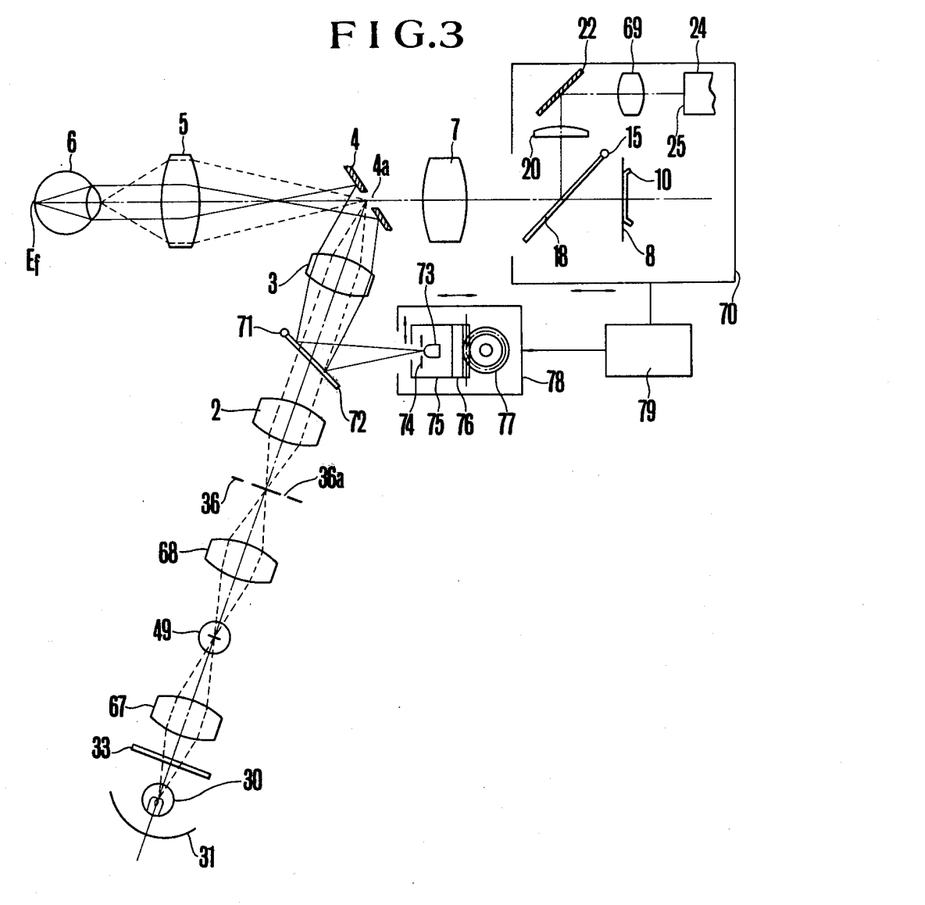
FIG. 3 shows yet another embodiment of the present invention.

FIG. 3 shows another example of the eye fundus camera. In the case of this example, the tungsten tube 30 and the speed light tube 49 are arranged in a tandem way. Namely, the tungsten tube 30 is provided at the center of the curvature of the concave mirror 31 while the speed light tube 49 is provided at the position at which the image of the tube 30 is formed by means of the condenser lens 67 and the slit plate 36 presenting a ring slit 36a is provided at the position at which the image of the speed light tube 49 is formed by means of the condenser lens 68. A filter 33 allowing the passage of only the light beam in the range of the wave length of the ultra red and the near ultra red ray is provided between the tube 30 and the lens 67. At the time of the observation of the eye fundus, the tube 30 is switched on and the ultra red ray reflected at the eye fundus Ef of the eye 6 to be inspected reaches the pick up tube 24 sensitive only to the light beam in the range of the ultra red ray, after having being reflected by the movable mirror 18. The relay lens 69 serves to form the image of the eye fundus on the field 20 lens by means of the ultra red ray again on the photoelectric converting plane 25 of the pick up tube 24 through the mirror 22.

At the time of the exposure of the film 8, the mirror 18 is raised up by means of the driving shaft 15, while the speed light tube 49 issues the visible light.

Further, the focussing is carried out by moving to and fro along the optical axis of the lens 5 the casing 70, in which the film holding means 10, the pick up tube 24 and so on are built, by means of a similar mechanism as explained in accordance with FIG. 20.

Between the collimating lens 2 and the relay lens 3, a filter 72 is slantly provided in slanted fashion so as to allow the passage of the light beam in the range of the ultra red ray and to reflect the visible light at the time of the observation of the eye fundus by means of the monitor. In the same way as in the case of the movable mirror, in the case of the conventional single reflex camera, the filter is withdrawn out of the light path of the illumination light beam by means of the rotation of the driving shaft 71 at the time of the exposure of the film 8. When the light amount of the illumination light beam is sufficient enough, the conventional half-mirror can be provided slantly in the light path instead of the filter 72.

Figure 13A:
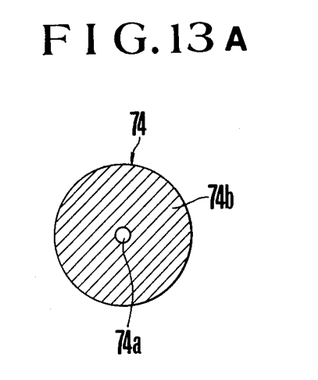
FIG. 13A and FIG. 13B show respectively another example of the visible target used in the embodiment of the present invention.

In the one light path divided by the filter 72, a small hole plate, behind which the light source 73 such as light emissive diodes radiating weak visible light, the tungsten tube and so on are provided, is provided at the position at which the image of the eye fundus of the eye to be inspected is formed by means of the objective lens 5, and the relay lens 3. As to the small hole plate 74, a small opening 74a is provided at the center of the shading part 74b as is shown in FIG. 13A. The light source 73 is lighted up when the photographic positions of the eye fundus are determined.

In order to orient the visual line of the eye 6 to be inspected along different directions in accordance with necessity, the casing including the lamp 73 and the small hole plate 74 is moved along the direction across the optical axis of the light reflected by the filter 72 seen from the side of the lens 3 by means of a mechanism including the rack 76 fixed on the casing 75 and the pinion 77 engaged with the rack 76. Namely with the rotation of the pinion 77 the small opening 74a of the plate 74 can be translated into the desired position, whereby when the eye to be inspected observes it, the photographs as is shown in FIGS. 15A, 15B and 15C can be taken.

Figure 13B:
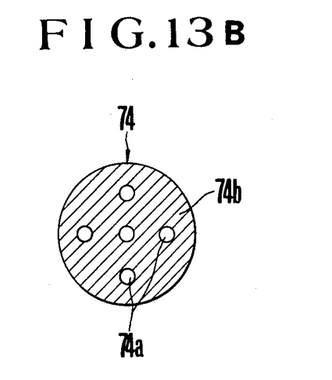

In order to eliminate such a translation mechanism as explained above, the small hole plate 74 can be replaced with a plate on whose shading part 74b a plural number of the small opening 74a are provided, as is shown in FIG. 13B. In this case, the instruction has to be given to the patient as to which small opening he has to observe in order to direct the visual line of the patient along the direction corresponding to the small opening.

Further in order that the patient can observe the target always clearly, the casing 77 including the members 73 - 77 is so designed as to be translated in the direction along the optical axis of the light reflected by the above mentioned filter 72, being in functional engagement of the movement of the casing 70, by means of the focus adjusting mechanism 79 including the rack, the pinion and the gear train as explained in accordance with FIG. 2, in such a manner that the small hole plate 74 is always situated exactly at the position conjugate to the eye fundus Ef.

Figure 4:
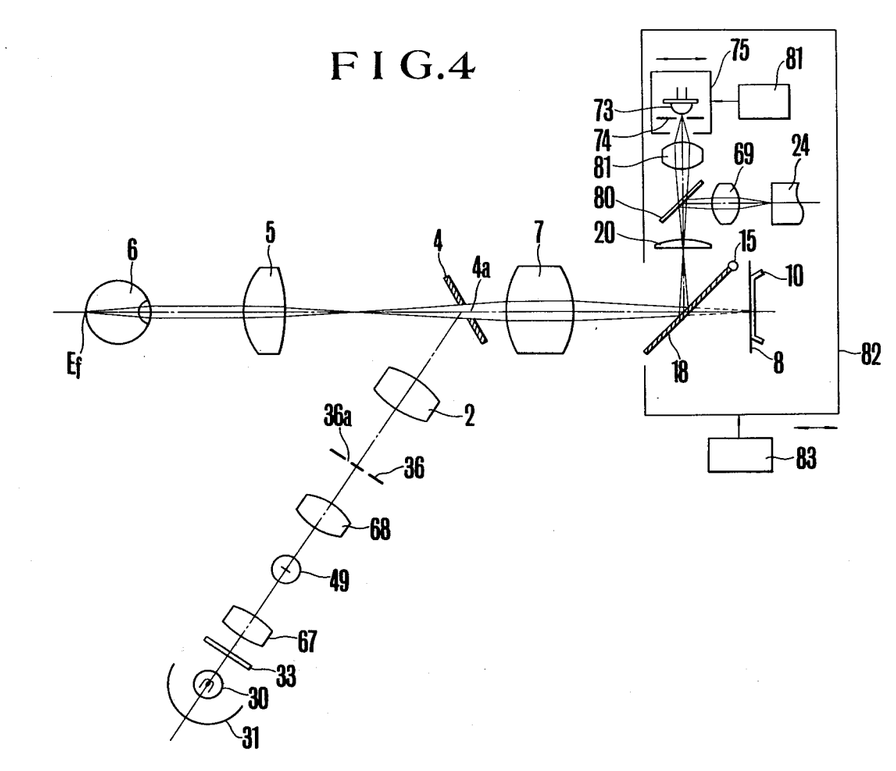
FIG. 4 shows a still further embodiment of the present invention.

In FIG. 4, a filter 80 which allows the passage of the visible light but reflects the ultra red ray is provided slantly between the field lens 20 and the relay lens 69. In the optical path of the light beam passing through the filter 80, a relay lens 81 is provided while a plate 74 with a small hole is provided at the position at which the image of the eye fundus Ef of the eye 6 to be inspected is formed by the object lens 5, the relay lenses 7 and 81. Behind the small hole plate 74, a visible light source 73 is provided. The casing 75 including the small hole plate 74 and the light source 73 is moved and adjusted by means of the same rack and pinion mechanism 81 as explained in accordance with FIG. 3 in such a manner that the small hole plate 74 moves along the direction across the optical axis of the lens 81 so as to orientate the visual line of the eye to be inspected in different directions. When hereby such plate as is shown in FIG. 13B as the plate 74, the mechanism 81 can be eliminated. The focussing of the optical system to the eye fundus can be carried out by moving the casing 82 including the film holding member 10, the pick up tube 24, the casing 75 and so on to and from in the direction along the optical axis of the lens 7 by means of the rack-pinion mechanism 83 in the same way as explained in accordance with FIG. 2.

Figure 5:
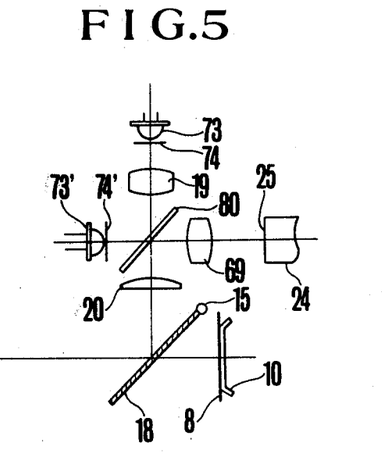
FIG. 5 shows an improvement of the embodiment shown in FIG. 4.
Figure 6:
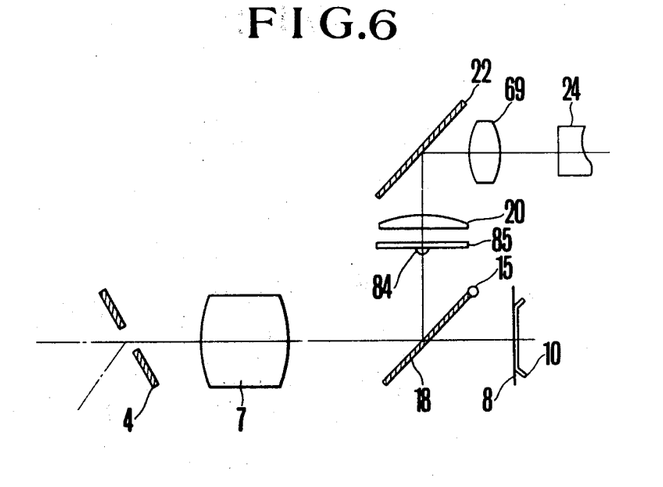
FIG. 6 shows the important part of the other embodiment of the present invention.
Figure 14:
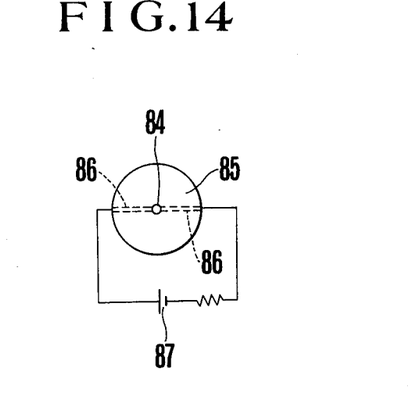
FIG. 14 shows further another example of the visible target used in the embodiment of the present invention.

In the case of the embodiment shown in FIG. 4, it is difficult to confirm the position of the target by means of the monitor. In FIG. 5, a target for observing the monitor is provided. On the plane of the photoconductive surface 25 of the pick up tube 24 on which an image is formed by means of the lens 69 with the visible light passing through the filter 80, a small hole plate 74' is provided whereby behind the plate 74' a visible light source 73' is provided. When the plates 74 and 74' respectively present only one small hole as is shown in FIG. 13A, they are so designed as to be moved and adjusted along the direction across their respective optical path by means of rack-pinion mechanisms as is shown in FIG. 3. Thus these two rack-pinion mechanisms are connected with each other by means of the mechanical power transmission means such as gear trains so as to move the plates 74 and 74' in such a manner that the position of the image of the small hole in the plate 74 on the eye fundus Ef is equivalent to the position of the image of the small hole in the image of the eye fundus on the photoconductive surface 25. In FIG. 6, the target 84 like light emissive diode is fixed on a transparent holding plate 85 and provided at the position near the field lens 20 at which the image of the eye fundus Ef is formed by means of the objective lens 5 and the relay lens 7. The light emissive diode 84 is connected to the current source 87 through the conductive route transparently metalized on the transparent holding plate 85 as is shown in FIG. 14. Thus no conductor is displayed on the monitor. When hereby only one diode is fixed on the transparent holding plate 85 as is shown in FIG. 14, the holding plate 85 is designed so as to be moved along the direction across the optical path by means of a rack-pinion mechanism as is shown in FIG. 3. When on the other hand, on a transparent holding plate 85 a plural number of the light emissive diodes are provided in a proper interval from each and they are switched on and off by means of the control means as is shown in FIG. 12, it is sufficient that the plate is fixed in the optical path.

Figure 7:
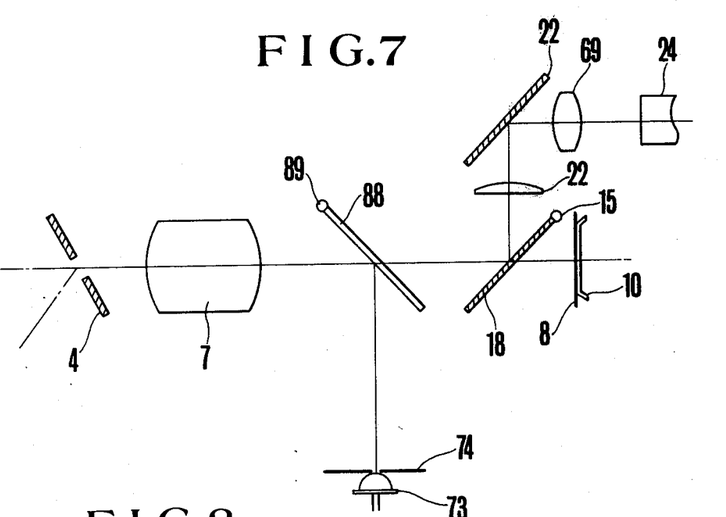
FIG. 7 shows the important part of another embodiment of the present invention.

In FIG. 7, a filter 88 which allows the passage of the ultra red ray but reflects the visible light is slantly provided between the relay lens 7 and the movable mirror 18. The filter 88 is brought out of the photographic optical path by means of the driving shaft 89 at the time of the exposure of the film 8. When a conventional half-mirror is used as the member 88, it can be fixed slantly in the optical path. At the position at which the image of the eye fundus Ef is formed by means of the objective lens 5 and the relay lens 7 with the one optical path divided by the filter 88 a small hole plate 74 as is shown in FIG. 13A or FIG. 13B is provided, whereby a visible light source 73 is provided behind the plate 74. When a plate with only one hole is used as the small hole plate 74, the plate is so designed as to be moved by means of a moving means like the rack-pinion mechanism as is explained in accordance with FIG. 3 in the direction across the optical path. When a plate with plural number of small holes is used, it can be fixed in the optical path. Hereby the focussing of the optical system to the eye fundus Ef is carried out by moving the optical system of the relay lens 7 at the other side of the eye 6 to be engaged to and fro along the optical axis of the lens 7 by means of a moving means like the rack-pinion mechanism as is shown in FIG. 2. In FIGS. 5, 6 and 7, a part of the optical system is eliminated, whereby the similar optical system as is shown in FIG. 4 is used as the optical system for illuminating the eye fundus and that for exposing the film.

In the optical systems shown in FIGS. 1 and 2, the targets shown in FIGS. 13A, 13B and 13C are used, while in the optical systems shown in FIGS. 3, 4, 5, 6 and 7, the targets shown in FIGS. 9 and 10 are used.

The described embodiments relates to a camera of the type in which the eye fundus is illuminated with the ultra red ray for observing the eye fundus at the time of focussing and determining the photographic positions, the image of the eye fundus with the ultra red ray is converted into a visible image by means of a monitor system for observation and the film is exposed, whereby the present invention can be applied not only to the camera of the type in which the pupil of the eye to be inspected is compulsorily delated by means of an agent, the operator directly observes the image of the eye fundus through the eye piece of the view finder so as to determine the photograhic position by illuminating the eye fundus by means of the visible light and then the film is exposed, but also to the camera of the type in which the eye fundus is illuminated with a visible but very weak light so as not to give any irritation to the eye to be inspected, the thus obtained image of the low brightness is amplified by means of an image intensifier, the thus intensified image of the eye fundus is observed so as to determine the photographic positions and then the film is exposed or to the optical instrument of the type in which the image of the eye fundus is only observed by means of the monitor, the eye-piece and so on, the film exposure means being not provided.

What is claimed is:

1. An optical instrument for examining the eye fundus comprising:
   an imaging lens system for forming the image of the eye fundus of the eye to be inspected, said system including an objective lens system optically opposite to the eye to be inspected;
   an image inspection means for examining the image of the eye fundus; and
   a visual line guide means for guiding the visual line of the eye to be inspected along the direction corresponding to the desired part of the eye fundus to be inspected, said means including a visible target being located at the position substantially conjugate to the eye fundus of the eye to be inspected, in the optical path of the light beam passing through the objective lens system of the imaging lens system.

2. An optical instrument in accordance with claim 1, wherein the visual line guide means includes a plural number of visible targets provided at the corresponding positions along the direction across the optical path.

3. An optical instrument in accordance with claim 2, wherein the plural number of the visible targets are visible light emissive while the visual line guide means further includes a control means for controlling the emission of the visible light of each visible target.

4. An optical instrument in accordance with claim 1, wherein the visual line guide means includes a means for moving the visible targets along the direction across the optical path in such a manner that the visual line of the eye to be inspected can be varied.

5. An optical instrument in accordance with claim 1, wherein the visual line guide means includes a means for varying the distance between the visible targets and the objective lens system in such a manner that the visible targets can be located at a position conjugate to the eye to be inspected in accordance with the visibility of the eye to be inspected.

6. An optical instrument in accordance with the claim 1, wherein the image inspection means includes a photosensitive body arranging means for arranging the photosensitive body for recording the image of the eye fundus formed by means of the imaging lens system.

7. An optical instrument for examining the eye fundus comprising:
   an objective lens system optically opposite to the eye to be inspected, said system forming the first image of the eye fundus of the eye to be inspected;
   a relay lens system for forming the second image, namely the image of the first image of the eye to be inspected;
   an image inspection means for inspecting the second image;
   an optical path branching optical system for forming branched optical paths by branching the optical path between the objective lens system and the relay lens system; and
   a visual line guide means for guiding the visual line of the eye to be inspected along the direction corresponding to the desired part of the eye fundus to be inspected, said means including at least one visible target provided at the position substantially conjugate to the eye fundus of the eye to be inspected in the branched optical path.

8. An optical instrument in accordance with claim 7, wherein the visual line guide means includes a plural number of visible targets provided at the corresponding positions along the direction across the optical path.

9. An optical instrument in accordance with claim 8, wherein the plural number of the visible targets are visible light emissive while the visual line guide means further includes a control means for controlling the emission of the visible light of each visible target.

10. An optical instrument in accordance with claim 7, wherein the visual line guide means includes a means for moving the visible target along the direction across the optical path in such a manner that the visual line of the eye to be inspected can be varied.

11. An optical instrument in accordance with claim 7, wherein the visual line guide means includes a means for varying the distance between the visible targets and the objective lens system in such a manner that the visual targets can be located at the position conjugate to the eye to be inspected in accordance with the visibility of the eye to be inspected.

12. An optical instrument in accordance with claim 7, wherein the image inspection means includes a photosensitive body arranging means for arranging the photosensitive body for recording the image of the eye fundus formed by means of the imaging lens system.

13. An optical system for examining the eye fundus comprising:
   an imaging lens system for forming the image of the eye fundus of the eye to be inspected;
   a photosensitive body arranging means for recording the image of the eye fundus;
   an optical path branching optical system for forming the branches optical path by branching the optical path between the imaging lens system and the plane on which a photosensitive body is arranged; and
   a visual line guide means for guiding the visual line of the eye to be inspected along the direction corresponding to the desired part of the eye fundus to be inspected, said means including at least one visible target at the position substantially conjugate to the eye fundus of the eye to be inspected.

14. An optical instrument in accordance with claim 13, wherein the visual line guide means includes a plural number of visible targets provided at the corresponding position along the direction across the optical path.

15. An optical instrument in accordance with claim 14, wherein the plural number of the visible targets are visible light emissive while the visual line guide means further includes a control means for controlling the emission of the visible light of each visible target.

16. An optical instrument in accordance with claim 13, wherein the visual line guide means includes a means for moving the visible targets along the direction across the optical path in such a manner that the visual line of the eye to be inspected can be varied.

17. An optical instrument in accordance with claim 13, wherein the visual line guide means includes a means for varying the distance between the visible targets and the objective lens system in such a manner that the visible target can be located at a position conjugate to the eye to be inspected in accordance with the visibility of the eye to be inspected.

18. An optical instrument in accordance with claim 13, wherein the image inspection means includes a photosensitive body arranging means for arranging the photosensitive body for recording the image of the eye fundus formed by means of the imaging lens system.

* * * * *